United States Patent
Bergeron, Jr.

(10) Patent No.: US 6,664,270 B2
(45) Date of Patent: *Dec. 16, 2003

(54) METHOD AND COMPOSITION FOR TREATMENT OF IRRITABLE BOWEL DISEASE

(75) Inventor: Raymond J. Bergeron, Jr., Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/209,638

(22) Filed: Aug. 1, 2002

(65) Prior Publication Data

US 2003/0153582 A1 Aug. 14, 2003

Related U.S. Application Data

(62) Division of application No. 09/987,694, filed on Nov. 15, 2001, now Pat. No. 6,458,795.

(51) Int. Cl.$^7$ .................... A61K 31/445; A61K 31/505; A61K 31/135; A61K 31/13
(52) U.S. Cl. ................ 514/316; 514/256; 514/646; 514/663; 514/667; 514/668
(58) Field of Search .................. 514/256, 316, 514/646, 663, 667, 668

(56) References Cited

U.S. PATENT DOCUMENTS

| | | |
|---|---|---|
| 4,239,768 A | 12/1980 | Rasmussen |
| 4,562,188 A | 12/1985 | Kuhla et al. |
| 4,701,457 A | 10/1987 | Yelnosky et al. |
| 4,745,131 A | 5/1988 | Yelnosky et al. |
| 4,843,074 A | 6/1989 | Rzeszotarski et al. |
| 4,877,779 A | 10/1989 | Rzeszotarski et al. |
| 4,970,207 A | 11/1990 | Sato et al. |
| 5,043,447 A | 8/1991 | Pascal et al. |
| 5,342,945 A | 8/1994 | Bergeron |
| 5,393,757 A | 2/1995 | Bergeron, Jr. et al. |
| 5,455,277 A | 10/1995 | Bergeron |
| 5,462,970 A | 10/1995 | Bergeron, Jr. et al. |
| 5,472,943 A | 12/1995 | Crain et al. |
| 5,510,390 A | 4/1996 | Bergeron, Jr. |
| 5,512,578 A | 4/1996 | Crain et al. |
| 5,580,876 A | 12/1996 | Crain et al. |
| 5,585,348 A | 12/1996 | Crain et al. |
| 5,677,352 A | 10/1997 | Bergeron, Jr. et al. |
| 5,767,125 A | 6/1998 | Crain et al. |
| 5,827,894 A | 10/1998 | Bergeron |
| 5,866,613 A | 2/1999 | Bergeron |
| 5,962,533 A | 10/1999 | Bergeron, Jr. |
| 6,034,139 A | 3/2000 | Bergeron |
| 6,147,262 A | 11/2000 | Bergeron |
| 6,184,232 B1 | 2/2001 | Bergeron, Jr. |
| 6,235,794 B1 | 5/2001 | Bergeron, Jr. |
| 6,262,125 B1 | 7/2001 | Bergeron, Jr. |
| 6,274,630 B1 | 8/2001 | Bergeron, Jr. |
| 6,297,287 B1 | 10/2001 | Bergeron, Jr. |
| 6,458,795 B1 * | 10/2002 | Bergeron, Jr. ............... 514/256 |

OTHER PUBLICATIONS

American Gastroenterological Association (AGA) Medical Position Statement: Irritable Bowel Syndrome. Gastroenterology 112:2118–2119 (1997).

Drossman D.A., Whitehead W.E., Camilleri M., "Irritable bowel syndrome: a technical review for practice guideline development", Gastroenterology 112:2120–2137 (1997)).

Snape W.J. Jr., "Irritable bowel syndrome", In: Bockus Gastroenterology, 5$^{th}$ edition W.S. Haubrich, F. Schoffner, ed.) Philadelphia: W.B. Saunders, pp. 1619–1636 (1995).

Dalton, C. and Drossman, D.A., Am. Fam. Physician 1997 55(3):875–880.

Camilleri, M. and Choi, M.–G., Aliment Pharmacol Ther 1997 11(1):3–15).

Drossman, D.A. et al., Gastroenterology 1988 95:701–708; Gaynes BN, Drossman D.A.: The role of psychosocial factors in irritable bowel syndrome. Baillieres Best Prac Res Clin Gastroenterol 13:437–452, 1999.

Jones J., Boorman J., Cann P., Forbes A., Gomborone J., Heaton K., Hungin P., Libby G., Spiller R., Read N., Silk D., Whorell P.: British society of gastroenterology guidelines for the management of the irritable bowel syndrome. Gut 47:ii 1 –ii 19, 2000.

Drossman, D.A., Dig Dis Sci 1993 38:1569–1580.

Talley, N.J. et al., Gastroenterology 1995 109:1736–1741.

K.B. Klein, Controlled treatment trials in the irritable bowel syndrome: a critique, Gastroenterology 95:232–241, 1988.

Dietary fiber, food intolerance, and irritable bowel syndrome, Nutrition Reviews 48: 343–346, 1990.

(List continued on next page.)

Primary Examiner—Raymond Henley, III
(74) Attorney, Agent, or Firm—Miles & Stockbridge P.C.; Dennis P. Clarke

(57) ABSTRACT

A method and composition for treating irritable bowel syndrome in a subject in need of such treatment, utilizing an amount of a polyamine having the formula:

$$RNH-(CH_2)_aNH(CH_2)_bNH(CH_2)_cNH_2, \quad\quad 1)$$

$$CF_3-C_6H_5-(CH_2)_a-NH-(CH_2)_b-NH-(CH_2)_c-NH-(CH_2)_d-NH-(CH_2)_e-C_6H_5-CF_3, \quad\quad 2)$$

$$R-NH-(CH_2)_a-NH-C_6H_6-NH-(CH_2)_b-NH-R \text{ and} \quad 3)$$

$$PIP-(CH_2)_aNH-(CH_2)_b-NH-(CH_2)_c-PIP, \quad\quad 4)$$

wherein:
R is alkyl, aryl, aralkyl, alkaryl, or cyclo-alkyl having up to about 10 carbon atoms, and any of the alkyl chains may optionally be interrupted by at least one etheric oxygen atom,
PIP is piperidine and
a, b, c, d, and e may be the same or different and are integers from 1–10 effective to treat irritable bowel syndrome.

11 Claims, No Drawings

OTHER PUBLICATIONS

W.L. Hasler and C. Owyang, Irritable bowel syndrome, In: Textbook of Gastroenterology, Ed. by T. Yamada, J.B. Lippincott Company, Philadelphia, Pa., 1696–1714 (1991).

M.M. Schuster, Irritable bowel syndrome, In: Gastrointestinal Disease, Pathophysiology Diagnosis and Management, Fourth Edition, Ed. by M.H. Sleisenger, J.S. Fordtran, W.B. Sunders Company, Philadelphia, Pa., 1402–1418 (1989).

W.S. Haubrich Irritable bowel Syndrome, Gastroenterology, Fourth Edition, Ed. by J.E. Berk, W.B. Saunders Company, Philadelphia, Pa., 2425–2444 (1985).

Jones J., Boorman J., Cann P., Forbes A., Gomborone J., Heaton K., Hungin P., Kumar D., Libby G., Spiller R., Read N., Silk D., Whorwell P: British society of gastroenterology guidelines for the management of the irritable bowel syndrome. Gut 47:ii 1 –ii 19, (2000).

Committee, Gastroenterology 1997 112:2120–2137; Pace, F. et al., Digestion 1995 56:433–442.

Chami, T.N., Am J Gastroenterol 1993 88:1568 (abstract).

Joshi et al., Anesthesiol. 1999, 90(4): 1007–11.

Konieczko, K.M. et al., Br J Anaesth 1988 61(3):313–23.

Dapoigny, M. et al., Dig Dis Sci 1995 40(10):2244–9.

Gue M., et al., Gastroenterology 1994 107(5):1327–34.

Wang, L. and Gintzler, A.R., Jneurochem 1995 64(3):1102–6.

Crain, S.M. and Shen, K.–F., Proc Natl Acad Sci USA 1995 92:10540–10544.

Crain, S.M., and Shen, K.–F., Trends Pharmacol Sci 1998 19:358–365.

Ann N Y Acad Sci 1998 845:106–25.

Shen, K.–F. and Crain, S.M., Brain Res 1997 757(2):176–90.

Joshi et al., Anesthesiol. 1999, 90(4): 1007–11.

Gan, T.J. et al., Anesthesiol. 1997 87:1075–1081.

Slepoy V.D., Stella M., Pezzotto S.M., Kraier L., Burde L., Wohlwend K., Razzari E., Polento L.; Irritable bowel syndrome clinical and psychopathological correlations; Dig Dis Sci 44:1008–1012, 1999.

Schmnulson M.W., Chang L.: Diagnostic approach to the patient with irritable syndrome; Am J Med 107:20S–26S, 1999.

Gaynes B.N., Drossman D.A.: The role of psychosocial factors in irritable bowel syndrome; Baillieres Best Prac Res Clin Gastroenterol 13:437–452, 1999.

Jones J., Boorman J., Cann P., Forbes A., Gomborone J., Heaton K., Hungin P., Kumar D., Libby G., Spiller R., Read N., Silk D., Whorwell P.: British Society of Gastroenterology guidelines for the management of the irritable bowel syndrome; Gut 47:ii 1 –ii 19, 2000.

Collins S.M., Vallance B., Barbara G., Borgaonkar M.: Putative inflammatory and immunological mechanisms in functional bowel disorders; Baillieres Best Prac Res Clin Gastroenterol 13:429–436, 1999.

Farthing M.J.; Irritable bowel syndrome: New pharmaceutical approaches to treatment; Baillieres Best Prac Res Clin Gastroenterol 13:461–471, 1999.

Tansy M.F., Martin J.S., Landin W.E., Kendall F.M., Melamed S.: Spermine and spermidine as inhibitors of gastrointestinal motor activity; Surg Gyn Obst 154:74–80, 1982.

Melamed S., Carlson G.R., Moss J.N., Belair E.J., Tansy M.R..; GI pharmacology of polyethyleneimine I: Effects on gastric emptying in rats; J. Pharm Sci 66:899–901, 1977.

Tansy M.F., Martin J.S. Innes D.L., Kendall F.M., Mellamed S., Moss J.N.; GI pharmacology of polyethylieneimine II: Motor activity in anesthetized dogs; J Pharm Sci 66:902–904, 1977.

Belair E.J., Carlson G.R., Melamed S., Moss J.N., Tansy M.R.; Effects of spermine and spermidine on gastric emptying in rats; J Pharm Sci 70:347, 1981.

Bergeron, R.J., Yao G.W., Yao H., Weimar W.R., Sninsky C.A., Raisler R., Feng Y., Wu Q., Gao F.; Metabolically programmed polyamine analogue antidiarrheals; J. Med Chem 39:2461–2471, 1996.

Tato T.L., Sninsky C.A., Bergeron R.J.; Structural specificity of synthetic analogues of polyamines and their effect on gastrointestinal motility. In Polyamines and the gastrointestinal tract, Falk Symposium, no 62. R.H Dowling, U.R. Folsch, C. Loser (eds), Boston, Kluwer Academic, 1991.

Sninsky C.A., Bergeron R.; Potent anti–diarrheal activity of a new class of compounds: Synthetic analogs of the polyamine pathway. Gastroenterology 104:A54, 1993.

Bergeron R.J., Weimar W.R., Luchetta G., Sninsky C.A., Wiegand J.; Metabolism and pharmacokinetics of $N^1,N^{14}$–diethylhomospermine. Drug Metab Dispos 24:334–343, 1996.

Bergeron R.J., Wiegand J., Weimar W.R., Snyder P.S., Porter C.W., Braylan R.C.; Chemical resection of the exocrine pancreas; Pancreas, 2001 –Submitted.

Bergeron R.J., Weimar W.R., Luchetta G., Streiff R.R., Wiegand J., Perrin J, Schreier K.M., Porter C., Dimova H.; "Metabolism and pharmacokinetics of $N^1,N^{11}$–diethylnorspermine", Drug Metab Dispos 23:117–1125, 1995.

Bergeron R.J., Wiegand J., McManis J.S., Weimar W.R., Smith R.E., Algee S.E., Fannin T.L., Slusher M.A., Snyder P.S.; "Polyamine analogue antidiarrheals: A structure–activity study". J Med Chem 44:232–244, 2001.

Bergeron R.J., McManis J.S., Liu C.Z., Feng Y., Weimar W.R., Luchetta G.R., Wu Q., Ortiz0Ocasio J., Vinson J.R.T., Kramer D., Porter C.; "Antiproliferative properties of polyamine analogues: A structure–activity study", J Med Chem 37:3464–3476, 1994.

Bergeron R.J., Feng Y., Weimar W.R., McManis J.S., Dimova H., Porter C., Raisler B., Phanstiel O.; "A comparison of structure–activity relationships between spermidine and spermine analogue antieneoplastics", J Med Chem 40:1475–1494, 1997.

Bergeron R.J., McManis J.S., Weimar W.R., Schreier K.M., Gao F., Wu Q., Ortiz–Ocasio J., Luchetta G.R., Porter C., Vinson J.R.T.; "The role of charge in polyamine analogue recognition", J Med Chem 38:2278–2285, 1995.

Bergeron et al., J Med Chem 44:232–244 (2001).

Almy T.P., Tulin M; "Alterations in colonic function in man under stress: Experimental production of changes simulating the irritable colon". Gastroenterology 8:616–626. 1947.

Drossman D.A., Powell D.W., Sessions J.T.; "The irritable bowel syndrome", Gastroenterology 73:811–822, 1977.

Narducci F., Snape W.J., Battle W.M., London R.L., Cohen S.; "Increased colonic motility during exposure to a stressful situation", Dig Dis Sci 30:40–44, 1985.

Tache Y., Monnikes H., Bonaz B., Rivier J.; "Role of CRF in stress–related alterations and colonic motor function", Ann N Y Acad Sci 697-233–243, 1993.

Kishibayashi N., Miwa Y, Hayashi H, Ishi A., Ichikawa S., Nonaka H., Yokoyama T., Suzuki F.; "5–HT3 receptor antagonists. 3. Quinoline derivatives which may be effective in the therapy of irritable bowel syndrome", J Med Chem 36:3286–3292, 1993.

Lenz H.J., Raedler A.S., Greten H., Vale W.W., Rivier J.E.; "Stress–induced gastrointestinal secretory and motor responses in rats are mediated by endogenous corticotroin-releasing factor", Gastroenterology 95:1510–1517, 1988.

Williams C.L., Villar R.G., Peterson J.M., Burks T.F.; "Stress–induced changes in intestinal transit in the rat: A model for irritable bowel syndrome", Gastroenterology 94:611–621, 1988.

Barone F.C., Deegan J.F., Price W.J., Fowler P.J., Fondacaro J.D., Ormsbee H.S.I; "A model of—stress–induced increased fecal output and colonic transit", Gastroenterology 90:AI337, 1986.

Barone F.C., Deegan W.J., Fowler P.J., Fondacaro J.D., Ormsbee H.S.I.; "Stress–induced diarrhea is not associated with abnormal gut secretion", Gastroenterology 90:AI337, 1986.

Barone F.C., Deegan J.F., Price W.J., Fowler P.J., Fondacaro J.D., Ormsbee H.S.I.; "Cold–resistant stress increases rat fecal pellet output and colonic transit", Am J Physiol 258:G329–G337, 1990.

Gue M., Junien J.L., Bueno L.; "Conditioned emotional response in rats enhances colonic motility through the release of corticotropin–releasing factor", Gastroenterology 100:964–970, 1991.

Bonaz B., Tache Y., "Water–avoidance stress–induced c–fos express in the rat brain and stimulation of fecal output: Role of a corticotropin–releasing factor", Brain Res 641:21–28, 1994.

Enck P., Merlin V., Erckenbrecht J.F., Weinbeck M.; "Stress effects on gastrointestinal transit in the rat", Gut 30:455–459, 1989.

Mormikes H., Schmidt B.G., Tache Y.; "Psychological stress–induced colonic transit in rats involves hypothalamic corticotropin–releasing factor", Gastroenterology 104:716–723, 1993.

Sninsky C.A., Broome T.A., Brooderson R.J., Bergeron R.J.; "Diethylhomospermine, a synthetic polyamine analog, prevents psychological stress–induced acceleration of colonic transit in rats", Gastroenterology 106:A569, 1994.

*Shiho Okano, et al. "Effects of TAK–637, a Novel Neurokinin–1 Receptor Antagonist, on Colonic Function in Vivo", The Journal of Pharmacology and Experimental Therapeutics, vol. 298, No. 2, pp 559–564, 2001.

*Seiji Kobayashi, et al., "Effects of YM905, a Novel Muscarinic $M_3$–Receptor Antagonist, on Experimental Models of Bowel Dysfunction in Vivo", Jpn. J. Pharmacol. 86, 281,288 (2001).

* cited by examiner

METHOD AND COMPOSITION FOR TREATMENT OF IRRITABLE BOWEL DISEASE

CROSS-REFERENCE TO RELATED APPLICATIONS

This is a divisional of application Ser. No. 09/987,694 filed Nov. 15, 2001, now U.S. Pat. No. 6,458,795.

BACKGROUND OF THE INVENTION

1. Field of the Invention

The present invention relates to pharmaceutical compositions and methods for the treatment of irritable bowel disease (IBD) [also termed: irritable bowel syndrome (IBS)]; more particularly for the treatment of diarrhea-predominant IBD.

2. Description of the Prior Art

Irritable bowel syndrome (IBS), a chronic or recurring gastrointestinal disorder, afflicts as many as 24% of women and 19% of men in the U.S., Europe, Japan, and China. IBS produces abdominal pain or discomfort in its victims and accounts for about one-eighth of primary care and more than one-fourth of gastroenterology practice. IBS has tremendous societal and economic impact since persons with IBS symptoms miss three times as many work days as those without and incur 70% higher health care costs. The American Gastroenterological Association has recently underscored the importance of IBS by issuing both a position statement (American Gastroenterological Association (AGA) Medical Position Statement: Irritable Bowel Syndrome. Gastroenterology 112:2118–2119 (1997)) and a technical review (Drossman D A, Whitehead W E, Camilleri M., "Irritable bowel syndrome: a technical review for practice guideline development", Gastroenterology 112:2120–2137 (1997)) on IBS. The description herein of IBS is based chiefly on these documents and on other current literature (such as that reviewed in Snape W J Jr., "Irritable bowel syndrome", In: Bockus Gastroenterology, 5th edition (W. S. Haubrich, F. Schoffner, ed.) Philadelphia: W. B. Saunders, pp. 1619–1636 (1995)).

IBS presents itself as abdominal pain accompanied by altered bowel habits. There is no established biological marker for IBS, which appears to result from faulty regulation in both the gastrointestinal and nervous systems. Once clinicians rule out other possible causes of IBS symptoms, they must devise a treatment plan based upon the severity and nature of the symptoms as well as other factors such as the degree of impairment the individual is experiencing in the activities of daily living. At present, treatment options range from education and dietary modification to drug therapy to psychological therapy. Drug and/or psychological therapy is called for in those 30% of IBS patients with moderate or severe symptoms. Given an IBS prevalence of 19% to 24%, IBS sufferers requiring such therapy represent 6–7% of the population at large, or well over 100 million individuals in continual need of such therapy in the U.S., Europe, Japan, and China.

While the symptoms of IBS have a physiological basis, no physiological mechanism unique to IBS has been identified. Rather, the same mechanisms that cause occasional abdominal discomfort in healthy individuals operate to produce the symptoms of IBS. The symptoms of IBS are therefore a product of quantitative differences in the motor reactivity of the intestinal tract, and increased sensitivity to stimuli or spontaneous contractions.

Due to a lack of readily identifiable structural or biochemical abnormalities in this syndrome, the medical community has developed a consensus definition and criteria, known as the Rome criteria, to aid in diagnosis of IBS. According to the Rome criteria, IBS is indicated by abdominal pain or discomfort which is (1) relieved by defecation and/or (2) associated with a change in frequency or consistency of stools, plus two or more of the following: altered stool frequency, altered stool form, altered stool passage, passage of mucus, and bloating or feeling of abdominal distention (Dalton, C. and Drossman, D. A., Am Fam Physician 1997 55(3):875–880). Thus, a hallmark of IBS is abdominal pain that is relieved by defecation, and which is associated with a change in the consistency or frequency of stools. IBS may be diarrhea-predominant, constipation-predominant, or an alternating combination of both.

Persons with IBS exhibit hypersensitivity, particularly hyperalgesia, in response to painful distensions in the small bowel and colon and to normal intestinal function. Furthermore, there are also increased or unusual areas of visceral pain. The abdominal pain is often poorly localized, and may be migratory and/or variable in nature. The pain may be worsened by meals and reduced upon defecation. Furthermore, IBS symptoms, including hyperalgesia, are commonly initiated or exacerbated by stress (Dalton, C. and Drossman, D. A., Am Fam Physician 1997 55(3):875–880).

Women apparently are more often affected than men, and the prevalence of irritable bowel syndrome is lower among the elderly (Camilleri, M. and Choi, M.-G., Aliment Pharmacol Ther 1997 11(1):3–15). It also seems clear that psychological factors, either stress or overt psychological disease, modulate and exacerbate the physiological mechanisms that operate in IBS (Drossman, D. A. et al., Gastroenterology 1988 95:701–708; Gaynes B N, Drossman D A: The role of psychosocial factors in irritable bowel syndrome. Baillieres Best Prac Res Clin Gastroenterol 13:437–452, 1999; Jones J, Boorman J, Cann P, Forbes A, Gomborone J, Heaton K, Hungin P, Kumar D, Libby G, Spiller R, Read N, Silk D, Whorwell P: British society of gastroenterology guidelines for the management of the irritable bowel syndrome. Gut 47:ii 1-ii 19, 2000). Some studies suggest that only about 10% to 50% of those afflicted with IBS actually seek medical attention. Nonetheless, IBS still accounts for up to about 3.5 million physician visits per year, and is the most common diagnosis in gastroenterologists' practice, accounting for about 25% of all patients (Camilleri and Choi, 1997). In a study published in 1993, persons afflicted with IBS were found to have more frequent doctor visits, a lower quality of life, and to miss three times as many days from work as those with no bowel symptoms (Drossman, D. A., Dig Dis Sci 1993 38:1569–1580). As a consequence, persons with IBS incur higher health care costs than those without IBS (Talley, N.J. et al., Gastroenterology 1995 109:1736–1741).

The AGA position statement recommends antispasmodic (anticholinergic) medication for IBS pain and bloating, or a tricyclic antidepressant or serotonin-selective reuptake inhibitor if the pain is severe. Dietary fiber is recommended (cisapride is also mentioned) for IBS constipation, whereas loperamide is recommended for diarrhea. For treatment of IBS patients presented with predominant diarrhea, the bile acid sequestrant "cholestyramine may be considered for a subgroup of patients with cholecystectomy or who may have idiopathic bile acid malabsorption." Clearly, there is no single pharmacologic treatment appropriate to all IBS sufferers. However, it is equally clear that it is acceptable clinical practice to employ a bile acid sequestrant to treat diarrhea associated with IBS.

The technical review issued by the AGA states that treatment with the bile acid sequestrant "cholestyramine should be considered in patients with IBS who have predominant diarrhea." Cholestyramine, a copolymer of styrene and divinylbenzene possessing trimethylbenzylammonium groups, has a somewhat limited capacity to bind bile acids, so very large quantities (as much as 20 grams per day) must be ingested in order to alleviate symptoms.

There is presently no effective treatment for irritable bowel syndrome (K. B. Klein, Controlled treatment trials in the irritable bowel syndrome: a critique, Gastroenterology 95: 232–241, 1988). Although largely ineffective, current treatment is multifactorial and consists of stress management, diet, and drugs, in that order. The patient is reassured that the disease is not life threatening and is advised to reduce or eliminate any controllable stress in his or her life. Relaxation exercises and biofeedback may be attempted to alter the psychogenic components of the illness. With respect to diet, the patient is advised to avoid any food to which he or she possesses a known sensitivity with respect to exacerbating the problem. A high fiber diet, either insoluble wheat bran or soluble psyllium, is almost routinely recommended, but with little if any positive benefit (Dietary fiber, food intolerance, and irritable bowel syndrome, Nutrition Reviews 48: 343–346, 1990).

Numerous drugs have been tried for the treatment of irritable bowel syndrome, but none has demonstrated sufficient efficacy to be of practical benefit to most patients. Psychoactive drugs, such as anxiolytics and antidepressants, even if effective for a given patient, have very limited, short-term utility because of the high potential for addiction to and abuse of these agents. Antispasmodics and various antidiarrheal preparations have been used but, even if they are effective, long-term treatment is precluded by problems such as development of tolerance, toxicity, or abuse potential. Several excellent reviews examine in detail the symptomology, diagnosis, and treatment of irritable bowel syndrome. These include: W. L. Hasler and C. Owyang, Irritable bowel syndrome, In: Textbook of Gastroenterology, Ed. by T. Yamada, J. B. Lippincott Company, Philadelphia, Pa., 1696–1714 (1991); M. M. Schuster, Irritable bowel syndrome, In: Gastrointestinal Disease, Pathophysiology Diagnosis and Management, Fourth Edition, Ed. by M. H. Sleisenger, J. S. Fordtran, W. B. Saunders Company, Philadelphia, Pa., 1402–1418 (1989); W. S. Haubrich, Irritable bowel syndrome, Gastroenterology, Fourth Edition, Ed. by J. E. Berk, W. B. Saunders Company, Philadelphia, Pa., 2425–2444 (1985) and Jones J, Boorman J, Cann P, Forbes A, Gomborone J, Heaton K, Hungin P, Kumar D, Libby G, Spiller R, Read N, Silk D, Whorwell P: British society of gastroenterology guidelines for the management of the irritable bowel syndrome. Gut 47:ii 1-ii 19, (2000).

Numerous patents have claimed activities of various types represented as being effective for relieving irritable bowel syndrome symptoms. For the most part they relate to substances which possess spasmolytic activity and thereby decrease intestinal motility. U.S. Pat. Nos. 4,611,011, 4,701,457, and 4,745,131 disclose a series of amidinoureas which reduce intestinal motility and are useful for treating irritable bowel syndrome. 1-Azabicyclo[2.2.2]octan-3-yl-2-aryl-3-azacyclo-2-hydroxypropionates and their quaternary salts, which possess antispasmodic activity and are useful for treating irritable bowel syndrome, are disclosed in U.S. Pat. No. 4,843,074. Calcium channel antagonists exhibit muscle relaxing and antispasmodic activities. A series of substituted imidazolyl-alkyl-piperazine and diazepine derivatives, disclosed in U.S. Pat. No. 5,043,447, are calcium channel antagonists and may be useful as antispasmodics for treating irritable bowel syndrome. 2-Aminomethylalkynylalkyl-1,3-dithiane derivatives with calcium-channel blocking activity and potentially similar uses are disclosed in U.S. Pat. No. 4,877,779. A series of triazinone derivatives with spasmolytic activity for treating irritable bowel syndrome are disclosed in U.S. Pat. No. 4,562,188.

In addition to antispasmodic agents, compounds with other activities have been disclosed which may relieve the symptoms of irritable bowel syndrome. U.S. Pat. No. 4,239,768 discloses a series of arylimidazolidinylidene ureas which decrease the sensitivity of the bowel to distension and thereby relieve irritable bowel symptoms. U.S. Pat. No. 4,970,207 discloses a series of benzodiazepine derivatives which are cholecystokinin antagonists and which may be useful for a large number of medical indications which include irritable bowel syndrome.

Since diarrhea is one frequent component of irritable bowel symptomatology, anti-diarrheal agents have been used to treat this disease. Unfortunately, such agents tend to exacerbate the constipatory phase of the disease and are, therefore, of little practical, long-term benefit.

Attempts to treat IBS generally focus on either (1) treatments directed to the intestinal tract (so-called "end organ therapy") or (2) treatments directed to affective disorders mediated by the CNS which are associated with IBS (Farthing, M. J. G., Drugs 1998 56(1): 11–21). Among the former are gut transit accelerants, such as wheat bran, soluble fiber, and polycarbophil calcium, for constipation-predominant IBS; antidiarrheals, such as loperamide, diphenoxylate, and codeine phosphate, for diarrhea-predominant IBS; and anticholinergics and smooth muscle relaxants, such as cimetropium bromide, pinaverium bromide, octilium bromide, trimebutine, and mebeverine, for diarrhea-predominant IBS and abdominal pain. In addition, alterations in diet have been targeted for those patients with food sensitivities or food allergies.

The end organ therapy treatments for IBS have proved ineffective or contain inherent drawbacks that limit their usefulness. For example, while the gut accelerants are useful to accelerate gut transit, they also exacerbate abdominal pain and bloating. Likewise, while antidiarrheals, such as loperamide, are often effective in treating diarrhea-predominant IBS, they are ineffective in treating the additional symptoms associated with IBS, such as abdominal pain. As a consequence, end organ therapy often is limited to patients with mild or moderate symptoms.

The anticholinergics and smooth muscle relaxants are effective in relieving pain associated with IBS, although their effects on other symptoms associated with IBS is unclear (Committee, Gastroenterology 1997 112:2120–2137; Pace, F. et al., Digestion 1995 56:433–442). In addition, some of the most effective compounds in these classes are not available for use in the United States, since they have not been approved by the Federal Food and Drug Administration (Committee, 1997). Finally, dietary alterations are of limited utility for a small segment of IBS patients.

Central nervous system treatments have received attention as potential IBS therapies because of the well recognized link between affective disorders and IBS, and also because of the disturbances in bowel health that occurs in individuals with these disorders. The tricyclic antidepressants, such as amitriptyline, imipramine, and doxepin, are frequently used to treat IBS, due to the neuromodulatory and analgesic properties of these compounds, which are independent of their psychotropic effects. However, because of their psychotropic properties, administration of these drugs requires long-term care, and are usually only given to patients with severe or refractory symptoms, impaired daily function, and associated depression or anxiety attacks. Furthermore, the newer antidepressants, in particular the specific serotonin reuptake inhibitors, such as fluoxetine, serraline, and paroxetine, have not been shown to be more effective than the tricyclic antidepressants, although some anecdotal evidence suggests these compounds may have fewer side effects (Committee, 1997).

Nalmefene glucuronide, an opioid receptor antagonist, has been investigated as a treatment for constipation-predominant IBS (Chami, T. N., et al., Am J Gastroenterol 1993 88:1568 [abstract]). Over an eight-week period, eight patients received 16 mg nalmefene glucuronide three times a week. While the patients reported decreased transit time and increased stool frequency, nalmefene glucuronide did not reduce abdominal pain or bloating, and stool consistency was not improved. The present inventors believe that the failure of nalmefene to treat pain associated with IBS can be attributed to the fact that this study used a high dose of nalmefene which antagonizes both excitatory and inhibitory opioid receptor-mediated functions in the gut as well as in the CNS. This view is supported by recent evidence that 1,000-fold lower doses of nalmefene (ca. 15:g, IV) have been shown to markedly enhance morphine's analgesic potency (Joshi et al., Anesthesiol. 1999, 90(4): 1007–11), whereas doses of >0.5 mg markedly attenuate opioid analgesia (Konieczko, K. M. et al., Br J Anaesth 1988 61(3):318–23).

Recent reports of successful treatment of IBS patients with high doses of the kappa opioid agonist, fedotizine (30 mg, three times daily) (Dapoigny, M. et al., Dig Dis Sci 1995 40(10):2244–9; Gue, M. et al., Gastroenterology 1994 107(5):1327–34) may be due to masking of supersensitized excitatory opioid receptor activity in the gut by activation of inhibitory opioid receptor functions, analogous to methadone maintenance of opioid addicts. Supersensitized excitatory opioid receptor functions in the gut may also result in tolerance to the analgesic effects of endogenous opioids (Wang, L. and Gintzler, A. R., J Neurochem 1995 64(3):1102–6), which could account for the abnormal visceral pain associated with IBS.

U.S. Pat. No. 5,512,578 discloses that the analgesic potency of bimodally-acting opioid agonists can be enhanced, and the tolerance/dependence liability reduced, upon coadministration of ultralow doses of selective excitatory opioid receptor antagonists. As used herein, "excitatory opioid receptor antagonists" are compounds that bind to and inactivate excitatory opioid receptors, but not inhibitory opioid receptors, on neurons in the nociceptive pathways. Such selective excitatory opioid receptor antagonists include, when administered at appropriately low doses, naloxone, naltrexone, etorphine, and dihydroetorphine. The selective excitatory opioid receptor antagonists attenuate excitatory, but not inhibitory, opioid receptor functions in nociceptive (pain) pathways of the peripheral and central nervous systems. As a result, symptoms associated with activation of excitatory opioid receptors, such as anti-analgesia, hyperalgesia, hyperexcitability, physical dependence and/or tolerance effects, are blocked, whereas the analgesic effects of bimodally acting opioid agonists, which are mediated by the inhibitory opioid receptors, are unmasked and thereby enhanced (see Crain, S. M. and Shen, K.-F., Proc Natl Acad Sci U S A 1995 92:10540–10544; Crain, S. M. and Shen, K.-F., Trends Pharmacol Sci 1998 19:358–365; Ann N Y Acad Sci 1998 845:106–25; Shen, K.-F. and Crain, S. M., Brain Res 1997 757(2):176–90). The predictions based on these preclinical studies have been recently confirmed by clinical studies on postsurgical patients which demonstrated that cotreatment with morphine plus low-dose naloxone or nalmefene markedly enhanced the analgesic potency of morphine administered over 24-hour test periods (Joshi et al., Anesthesiol. 1999, 90(4): 1007–11; Gan, T. J. et al., Anesthesiol. 1997 87:1075–1081).

U.S. Pat. No. 5,512,578 further discloses that ultralow doses of naltrexone can, alone or in combination with low-dose methadone, provide effective longterm maintenance treatment for opioid addiction to prevent relapse to drug abuse. Furthermore, ultralow doses of selective excitatory opioid receptor antagonists can be administered alone to chronic pain patients to enhance the analgesic potency and reduce the tolerance/dependence liability of endogenous opioid peptides, such as enkephalins, dynorphins, and endorphins, which are elevated in chronic pain patients (Crain and Shen, 1995). However, there is no teaching or suggestion in U.S. Pat. No. 5,512,578 that administration of a selective excitatory opioid receptor antagonist would be useful in treating symptoms of IBS. In particular, there is no teaching or suggestion that administration of a selective excitatory opioid receptor antagonist would be useful in treating symptoms of IBS that are unrelated to the nociceptive pathways, such as stool frequency or consistency.

U.S. Pat. No. 5,472,943 also discloses a method wherein coadministration of an ultralow dose of a selective excitatory opioid receptor antagonist with a bimodally-acting opioid agonist selectively enhances the analgesic effect of the bimodally-acting opioid agonist while reducing the undesirable side-effects associated with longterm administration of the opioid agonist. However, U.S. Pat. No. 5,472,943 does not disclose that a selective excitatory opioid receptor antagonist can be used in the absence of a bimodally-acting opioid agonist.

Both U.S. Pat. Nos. 5,580,876 and 5,767,125 also disclose a method to selectively enhance the analgesic effect of a bimodally-acting opioid agonist while reducing unwanted side-effects associated with the administration of the opioid agonist by coadministration of the opioid agonist with an amount of an excitatory opioid receptor antagonist, such as naltrexone or nalmefene, effective to enhance the analgesic effect of the bimodally-acting opioid agonist while reducing the undesirable side-effects. U.S. Pat. Nos. 5,580,876 and 5,767,125 disclose use of an excitatory opioid receptor antagonist alone for treatment of opioid addicts, and do not teach or suggest that administration of a selective excitatory opioid receptor antagonist would be useful in treating symptoms of IBS. In particular, there is no teaching or suggestion that administration of a selective excitatory opioid receptor antagonist would be useful in treating other symptoms of IBS, such as stool frequency or consistency.

U.S. Pat. No. 5,585,348 relates to a method for reducing hyperalgesia associated with administration of nerve growth factor or related growth factors. The method comprises administration of a selective excitatory opioid receptor antagonist prior to or simultaneously with the administration of nerve growth factor. However, U.S. Pat. No. 5,585,348 does not disclose that the selective opioid receptor antagonist may be administered in the absence of nerve growth factor, and does not teach or suggest that the administration of a selective excitatory opioid receptor antagonist alone would be useful in treating IBS.

In spite of the many treatments and inventions devised to relieve or prevent irritable bowel syndrome, the unfortunate fact is that presently no suitable long term, safe and efficacious treatment or preventative is available for this troublesome and widespread disease.

It is an object of the invention to provide novel pharmaceutical compositions and methods for the long term, safe and efficacious treatment of irritable bowel disease (IBD) or syndrome (IBS).

SUMMARY OF THE INVENTION

The above and other objects are realized by the present invention, one embodiment of which relates to a method for treating irritable bowel syndrome in a subject in need of such treatment, comprising administering to the subject an amount of a polyamine effective to treat irritable bowel syndrome in the subject, the polyamine being selected from the group consisting of:

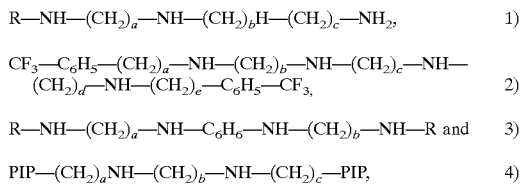

wherein:
R is alkyl, aryl, aralkyl, alkaryl, or cyclo-alkyl having up to about 10 carbon atoms, and any of the alkyl chains may optionally be interrupted by at least one etheric oxygen atom,
PIP is piperidine and
a, b, c, d, and e may be the same or different and are integers from 1–10.

Another embodiment of the invention concerns a pharmaceutical composition adapted for administration to a subject suffering from irritable bowel syndrome comprising a therapeutically effective amount of a polyamine as described above to treat irritable bowel syndrome and a pharmaceutically acceptable carrier therefor.

A still further embodiment of the invention comprises an article of manufacture comprising packaging material and a pharmaceutical agent contained within the packaging material, wherein the pharmaceutical agent is effective for the treatment of a subject suffering from irritable bowel syndrome, and wherein the packaging material comprises a label which indicates that the pharmaceutical agent can be used for ameliorating the symptoms associated with irritable bowel syndrome, and wherein the pharmaceutical agent is selected from the group consisting of polyamines having the formula:

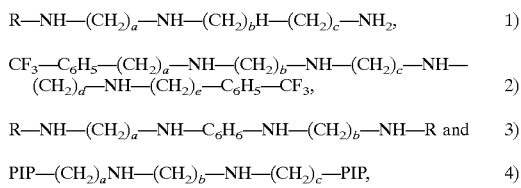

wherein:
R is alkyl, aryl, aralkyl, alkaryl, or cyclo-alkyl having up to about 10 carbon atoms, and any of said alkyl chains may optionally be interrupted by at least one etheric oxygen atom,
PIP is piperidine and
a, b, c, d, and e may be the same or different and are integers from 1–10.

DETAILED DESCRIPTION OF THE INVENTION

The invention arose out of research directed toward the evaluation of a group of polyamine analogues as agents to ameliorate diarrhea-predominant irritable bowel syndrome. Each compound was assessed when administered subcutaneously (SC) in a psychological stress-induced model of irritable bowel syndrome in rodents for its ability to reduce stool output in a dose-dependent manner. The spermine pharmacophore was found to be an excellent platform from which to construct compounds to treat irritable bowel syndrome. The activity of the compounds is critically dependent on both the nature of the terminal substituent groups and the geometry of the groups separating the nitrogens of the polyamines. In addition to the SC studies, several compounds, $N^1,N^{11}$-diethylnorspermine, $N^1,N^{12}$ diethylspermine, $N^1,N^{12}$ diisopropylspermine, $N^1,N^{14}$-diethylhomospermine, N,N'-bis[5-(ethylamino)pentyl]-4-butanediamine, N,N'-bis[2-(4-piperidinyl)ethyl]-1,4-diaminobutane, and N,N'-bis[3-(ethylamino)propyl]-trans-1,4-cyclohexanediamine, were subsequently evaluated for oral efficacy. The remarkable activity of N,N'-bis[3 (ethylamino)propyl]-trans-1,4-cyclohexanediamine led to further exploration of this framework as a pharmacophore for the construction of other analogues to relieve the symptoms of diarrhea-predominant IBS.

As noted above, Irritable Bowel Syndrome (IBS) is a chronic disorder that occurs in 15–20 percent of the US population and accounts for up to 50% of outpatient referrals to gastroenterologists (Slepoy V D, Stella M, Pezzotto S M, Kraier L, Burde L, Wohlwend K, Razzari E, Polento L: Irritable bowel syndrome clinical and psychopathological correlations. Dig Dis Sci 44:1008–1012, 1999). It is characterized by altered bowel function, i.e., constipation, diarrhea, or alternating constipation and diarrhea, with or without abdominal pain (Schmnulson M W, Chang L: Diagnostic approach to the patient with irritable bowel syndrome. Am J Med 107:20S-26S, 1999). Although the pathogenesis remains controversial, this malady is considered primarily a psychosocial or psychiatric disorder by some (Gaynes B N, Drossman D A: The role of psychosocial factors in irritable bowel syndrome. Baillieres Best Prac Res Clin Gastroenterol 13:437–452, 1999; Jones J, Boorman J, Cann P, Forbes A, Gomborone J, Heaton K, Hungin P, Kumar D, Libby G, Spiller R, Read N, Silk D, Whorwell P: British Society of Gastroenterology guidelines for the management of the irritable bowel syndrome. Gut 47:ii 1-ii 19, 2000), others have suggested immunological and inflammatory mechanisms (Collins S M, Vallance B, Barbara G, Borgaonkar M: Putative inflammatory and immunological mechanisms in functional bowel disorders. Baillieres Best Prac Res Clin Gastroenterol 13:429–436, 1999) or abnormalities of intestinal motility and/or enhanced visceral sensitivity (Gaynes, supra; Farthing M J: Irritable bowel syndrome: New pharmaceutical approaches to treatment. Baillieres Best Prac Res Clin Gastroenterol 13:461–471, 1999). Thus, it is possible that IBS may be managed by chemotherapeutic means, including using agents that modify intestinal motility (Gaynes, supra).

Tansy and co-workers, in a series of well-conceived studies, first demonstrated the striking impact of polyamines on the motility of the gastrointestinal (GI) tract (Tansy M F, Martin J S, Landin W E, Kendall F M, Melamed S: Spermine and spermidine as inhibitors of gastrointestinal motor activity. Surg Gyn Obst 154:74–80, 1982). The original work focused on poly(ethyleneimine) and gastric emptying.

Branched-chain poly(ethyleneimine)s effected significant inhibition of gastric emptying in rodents (Melamed S, Carlson G R, Moss J N, Belair E J, Tansy M R GI pharmacology of polyethyleneimine I: Effects on gastric emptying in rats. J Pharm Sci 66:899–901, 1977); however, their therapeutic potential was compromised by the observation that the same compounds elicited a severe retch response in dogs (Tansy M F, Martin J S, Innes D L, Kendall F M, Melamed S, Moss J N: GI phannacology of polyethyleneimine II: Motor activity in anesthetized dogs. J Pharm Sci 66:902–904, 1977). Nevertheless, because of the structural relationship between the poly(ethyleneimine)s and natural polyamines, the study moved forward; the effects of spermidine, spermine, and a group of polyamine analogues on the gastric emptying of rodents were also investigated (Belair E J, Carlson G R, Melamed S, Moss J N, Tansy M R Effects of spermine and spennidine on gastric emptying in rats. J Pharm Sci 70:347, 1981). It soon became apparent that polyamines had a considerable influence on gastric emptying and that "endogenous spermine and spermidine may have some unrecognized GI secretornotor activity" (Belair et al, supra). It also became obvious, from a structure-activity perspective, that minor alterations in the polyamine's structure could completely abolish the molecule's ability to inhibit gastric emptying. Thus, these studies strongly suggested that the polyamine pharmacophore was an excellent candidate for the construction of antitransit, antidiarrheal drugs.

For example, although $N^1,N^{11}$-diethylnorspermine [DENSPM; DE(3,3,3)], was ineffective in a rodent castor oil-induced diarrhea model (Bergeron R J, Yao G W, Yao H, Weimar W R, Sninsky C A, Raisler B, Feng Y, Wu Q, Gao F: Metabolically programmed polyamine analogue antidiarrheals. J Med Chem 39:2461–2471, 1996), the polyamine analogue predicated on a different backbone only three methylene units longer, $N^1,N^{14}$-diethylhomospermine [DEHSPM; DE(4,4,4)], is a very potent antidiarrheal as demonstrated in a number of animal models and in the clinic against AIDS-related diarrhea (Sato T L, Sninsky C A, Bergeron R J, Structural specificity of synthetic analogues of polyamines and their effect on gastrointestinal motility. In Polyamines and the gastrointestinal tract, Falk Symposium, no 62. R H Dowling, U R Folsch, C Loser (eds). Boston, Kluwer Academic, 1991; Sninsky C A, Bergeron R: Potent anti-diarrheal activity of a new class of compounds: Synthetic analogs of the polyamine pathway. Gastroenterology 104:A54, 1993). Unfortunately, the N-de-ethylated metabolite of DEHSPM, homospermine (HSPM), has a very protracted half-life, 2–3 weeks in mice and even longer in the dog (Bergeron R J, Weimar W R, Luchetta G, Sninsky C A, Wiegand J: Metabolism and pharmacokinetics of $N^1,N^{14}$-diethylhomospennine. Drug Metab Dispos 24:334–343, 1996). Each subsequent dose of DEHSPM results in a further accumulation of HSPM until toxic levels of the metabolite are reached. Furthermore, SC administration of DEHSPM to three dogs at a daily dose of 2 mg/kg for 11–17 days resulted in ventricular bigeminies. The arrhythmia was apparent in a 6-lead EKG as early as three days into the dosing period (Bergeron R J, Wiegand J, Weimar W R, Snyder P S, Porter C W, Braylan R C: Chemical resection of the exocrine pancreas. Pancreas:, 2001-Submitted).

It was then attempted to circumvent the accumulation of HSPM by assembling a dihydroxylated DEHSPM derivative, $(3R,12R)-N^1,N^{14}$-diethyl-3,12-dihydroxyhomospermine [(R,R)—(HO)$_2$DEHSPM]. The presence of the hydroxyl groups would, theoretically, yield a more metabolically labile compound. Indeed, this was found—(HO)$_2$DEHSPM was as effective an antidiarrheal as DEHSPM, yet its residence time in most mouse tissues was shorter than that of DEHSPM. In addition, the induction of cardiac bigeminies observed in (HO)$_2$DEHSPM-treated dogs was minimal. Unfortunately, when dogs were given (HO)$_2$DEHSPM at a dose of 4.3 mg/kg/day for 14 days or 2.15 mg/kg/d for 28 days, exocrine pancreatic insufficiency developed approximately 40 days post-final dose and became severe within an additional 14 days; histological analysis revealed that the acinar-derived exocrine pancreas was severely atrophied. Although the hydroxylated DEHSPM derivative considerably decreased stool output in a castor oil-induced diarrhea model in rats with little build-up of either drug or metabolite in most tissues of mice and dogs, its long-term toxicity profile is unacceptable; the problem of designing a metabolically labile polyamine analogue still remains.

Thus, DENSPM, DEHSPM and (HO)$_2$DEHSPM possess drawbacks as antidiarrheal agents. The former was more metabolically labile by virtue of its aminopropyl components, but was ineffective in reducing stooling; the latter two, although effective, were metabolically inert after de-ethylation to HSPM (DEHSPM) or caused exocrine pancreatic insufficiency [(HO)$_2$DEHSPM]. In the retrograde processing of both spermidine (SPD) and spermine (SPM), the aminopropyl ends of these systems are first acetylated by spermidine/spermine-$N^1$-acetyltransferase (SSAT); the nearest internal carbon-nitrogen bond is oxidized to an imine; and the imine is hydrolyzed to 3-acetamidopropanal and the corresponding amine. Spermine is thereby converted to SPD and a mole of 3-acetamidopropanal, and SPD yields putrescine and 3-acetamidopropanal. Since DENSPM contains aininopropyl moieties, it is processed by this mechanism to yield 3-acetamidopropanal, N-ethylnorspermine, N-ethylnorspermidine, N-ethyl-1,3-diaininopropane, norspermidine, and diaminopropane (Bergeron R J, Weimar W R, Luchetta G, Streiff R R, Wiegand J, Perrin J, Schreier K M, Porter C, Yao G W, Dimova H: Metabolism and pharmacokinetics of $N^1,N^{11}$-diethylnorspermine. Drug Metab Dispos 23:1117–1125, 1995).

Therefore, if dialkylated SPMs ameliorated diarrhea and were subsequently dealkylated, the issue of metabolite (i.e., SPM) build-up would not be problematic as with HSPM. The catabolic processing should be similar to what was observed with DENSPM. However, in this instance, three natural products-SPM, SPD, and putrescine-are generated. Thus, we investigated a series of SPM [(3,4,3)] analogues in a castor oil-induced diarrhea model (Bergeron R J, Wiegand J, McManis J S, Weimar W R, Smith R E, Algee S E, Fannin T L, Slusher M A, Snyder P S: Polyamine analogue antidiarrheals: A structure-activity study. J Med Chem 44:232–244, 2001). We found that the SPM backbone was an excellent framework from which to construct active antidiarrheals with acceptable toxicity profiles. The current work describes an assessment of a series of polyamine analogues for their ability to reduce psychological stress-induced fecal output in a rodent model of IBS and strongly suggests that the polyamine pharmacophore is a useful platform from which to construct therapeutics suitable for treatment of diarrhea-predominant IBS.

All of the polyamines and chemical compounds described herein are known in the prior art. The polyamines are described as well as methods for their preparation are described in U.S. Pat. Nos. 6,297,287; 6,274,630; 6,262, 125; 6,235,794; 6,184,232; 6,147,262; 6,034,139; 5,962, 533; 5,866,613; 5,827,894; 5,677,352; 5,510,390; 5,462, 970; 5,455,277; 5,393,757; 5,342,945; and Bergeron R J, McManis J S, Liu C Z, Feng Y, Weimar W R, Luchetta G R, Wu Q, Ortiz-Ocasio J, Vinson J R T, Kramer D, Porter C: Antiproliferative properties of polyamine analogues: A structure-activity study, J Med Chem 37:3464–3476, 1994; Bergeron R J, Feng Y, Weimar W R, McManis J S, Dimova H, Porter C, Raisler B, Phanstiel O: A comparison of structure-activity relationships between spermidine and spermine analogue antineoplastics. J Med Chem 40:14751494, 1997; Bergeron R J, McManis J S, Weimar W R, Schreier K M, Gao F, Wu Q, Ortiz-Ocasio J, Luchetta G R, Porter C, Vinson J R T: The role of charge in polyamine analogue recognition. J Med Chem 38:2278–2285, 1995; and Bergeron et al, J. Med Chem. 44:232–244 (2001), the entire contents and disclosures of all and each of which are incorporated herein by reference.

For the acute toxicity assessment the CHX(3,4,3)-trans was administered to female CD-1 mice (Charles River, Wilmington, Mass.) as a single intraperitoneal (IP) injection. The animals were carefully observed post-dosing and were scored 2 h after administration of the drug.

For drug preparation and administration, the compounds were put into solution with sterile normal saline and sonicated briefly, if necessary. The drugs were made up at concentrations such that the rats received the drugs PO or SC at the rate of I cc per kilogram. Mice received the CHX(3, 4,3)-trans IP at 1 cc per 100 grams. The solutions were made fresh the day of the study. Control animals received an equivalent amount of saline PO or SC.

IBS-like symptoms, e.g., increased myoelectric activity and colonic contractility, have been induced in healthy human volunteers by subjecting them to various forms of physical or psychological stress[Almy T P, Tulin M: Alterations in colonic function in man under stress: Experimental production of changes simulating the "irritable colon". Gastroenterology 8:616–626, 1947; Drossman D A, Powell D W, Sessions J T: The irritable bowel syndrome. Gastroenterology 73:811–822, 1977; Narducci F, Snape W J, Battle W M, London R L, Cohen S: Increased colonic motility during exposure to a stressful situation. Dig Dis Sci 30:40–44, 1985; Tache Y, Monnikes H, Bonaz B, Rivier J: Role of CRF in stress-related alterations and colonic motor function. Ann N Y Acad Sci 697:233–243, 1993]. Animal models of stress-associated motility disorders, e.g., irritable bowel syndrome, have included such stressors as partial or complete body restraint at room temperature (Kishibayashi N, Miwa Y, Hayashi H, Ishi A, Ichikawa S, Nonaka H, Yokoyama T, Suzuki F: 5-HT3 receptor antagonists. 3. Quinoline derivatives which may be effective in the therapy of irritable bowel syndrome. J Med Chem 36:3286–3292, 1993; Lenz H J, Raedler A S, Greten H, Vale W W, Rivier J E: Stress-induced gastrointestinal secretory and motor responses in rats are mediated by endogenous corticotropin-releasing factor. Gastroenterology 95:1510–1517, 1988; Williams C L, Villar R G, Peterson J M, Burks T F: Stress-induced changes in intestinal transit in the rat: A model for irritable bowel syndrome. Gastroenterology 94:611–621, 1988) or cold (Barone F C, Deegan J F, Price W J, Fowler P J, Fondacaro J D, Onnsbee H S I: A model of stress-induced increased fecal output and colonic transit. Gastroenterology 90:A1337, 1986; Barone F C, Deegan J F, Price W J, Fowler P J, Fondacaro J D, Ormsbee H S I: Stress-induced diarrhea is not associated with abnormal gut secretion. Gastroenterology 90:A1337, 1986; Barone F C, Deegan J F, Price W J, Fowler P J, Fondacaro J D, Onnsbee H S I: Cold-restraint stress increases rat fecal pellet output and colonic transit. Am J Physiol 258:G329–G337, 1990), a conditioned fear response caused by placing the rats into cages in which they had previously experienced inescapable footshocks (Gue M, Junien J L, Bueno L: Conditioned emotional response in rats enhances colonic motility through the release of corticotropin-releasing factor. Gastroenterology 100:964–970, 1991), or by exposing the animals to psychological stress involving passive avoidance of an aversive stimulus, water (Bonaz B, Tache Y: Water-avoidance stress-induced c-fos expression in the rat brain and stimulation of fecal output: Role of corticotropin-releasing factor. Brain Res 641:21–28, 1994; Enck P, Merlin V, Erckenbrecht J F, Weinbeck M: Stress effects on gastrointestinal transit in the rat. Gut 30:455–459, 1989; Mormikes H, Schmidt BG, Tache Y: Psychological stress-induced colonic transit in rats involves hypothalamic corticotropin-releasing factor. Gastroenterology 104:716–723, 1993; Sninsky C A, Broome T A, Brooderson R J, Bergeron R J: Diethylhomospermine, a synthetic polyamine analog, prevents psychological stress-induced acceleration of colonic transit in rats. Gastroenterology 106:A569, 1994).

Subjecting the rats to any of the above stressors results in an increase in colonic transit and fecal output similar to what was observed in the healthy human volunteers that were subjected to physical or psychological stress. Of these animal models, we chose the latter, psychological stress, to be used for the screening of a series of our synthetic polyamine analogues for their ability to minimize the stress-associated increase in fecal output.

Animal care and experimental procedures were approved by the Institutional Animal Care and Use Committee. Male Sprague-Dawley rats (250–350 g, Harlan Sprague-Dawley, Indianapolis, Ind.) were housed in polycarbonate cages in a temperature- and humidity-controlled room with a 12-hour light/dark cycle. The experiments were performed at the same time of the day to decrease diurnal variability. A typical experiment involved 20 rats: 5 saline-treated controls and 5 pretreated with polyamine analogues at each of three doses as either a SC injection or a PO gavage. The rats in the SC studies and in one set of experiments involving PO administration were allowed ad libitum access to a standard rodent diet and tap water until the morning of the experiment. Stress was initiated 30 minutes post drug as described below. In another set of experiments involving PO administration, the animals were fasted overnight but were allowed free access to water. The animals were then stressed from ½ h to 2 h post-drug (data not shown). In a final experiment, non-stressed control rats were injected with saline SC and housed in individual polycarbonate cages. The fecal output (number of pellets) of the stressed and unstressed animals was recorded at 30-min intervals for a 6-h period, during which they received no food or water.

Once the drug had been administered, the animals were housed individually in polycarbonate cages containing a clear 70×50 mm Pyrex crystallization dish (Fisher, Pittsburgh, Pa.) inverted in the center and held in place with vacuum grease. To initiate the stress, water was added to each cage to a depth of at least 4.5 cm, i.e., within 0.5 cm of the top of the Pyrex dish. To avoid contact with water, the rats stand on the glass dish for the 6 h of the study. Stool output was expressed as the total number of fecal pellets excreted over the 6-h collection period. Percent reduction was calculated by dividing the mean value from the treated animals (T) by the mean value from the control animals (C), subtracting the resulting quotient from 1.0, and multiplying by 100 [i.e., (1.0−T/C)×100].

A one-tailed t-test assuming unequal variance was performed on the stool output data of the treated vs control (0 mg/kg) animals for each compound. A value of $P<0.05$ was considered significant.

This structure-activity study was designed to identify the best platform from which to construct therapeutic agents for controlling diarrhea in IBS patients and was predicated on earlier work with many of these analogues as antidiarrheals. The first polyamine analogue that was found to be effective against both diarrhea and IBS was DEHSPM. Unfortunately, this compound displayed an unacceptable toxicity profile. Thus, our intent was to identify those structural components of the analogues responsible for the anti-IBS properties and partition them from the toxic fragments. Accordingly, DEHSPM was modified in three ways (Table 1): (a) changing the distance between the nitrogens and the overall length of the molecule [e.g., compounds 1, 3, and 14 versus DEHSPM], (b) altering the terminal alkyl groups within a series of compounds possessing the same backbone [e.g., DESPM (3) and compounds 4–11], and (c) keeping the overall length of the molecule the same but manipulating the ordering of the distance between the nitrogens (e.g., 16 versus 13).

The psychological stress-induced IBS model involves subjecting the rats to an aversive stimulus (water) and observing the increase in fecal output over a period of time. The compounds were generally administered SC at doses of 2.3, 11.6, 23.2, and 57.8:mol/kg, equivalent to 1, 5, 10, or 25 mg/kg of DEHSPM. Control rats received an equivalent amount of saline SC. The unstressed control rats (n=15) excreted 3.1+3.1 fecal pellets over the 6-h collection period. The stool output (number of pellets) for the stressed control and treated animals are in Table 1.

Compounds predicated on a (3,3,3) backbone (DENSPM, DIPNSPM) were ineffective at diminishing stress-induced fecal output (Table 1). Extending the backbone of the norspermine compounds by one methylene group in the center to yield the (3,4,3) SPM systems substantially enhanced the anti-IBS activity of the compounds. Furthermore, small alterations in the terminal alkyl groups of SPM analogues could also have a profound effect on the drug's anti-IBS properties (Table 1). Because the (3,4,3) analogues demonstrated generally good activity, the comparison among them is best made at intermediate doses. In the IBS model at the 23.2:mol/kg dose, DESPM (3) significantly reduced stress-elicited stooling by 35% (P<0.001). At the same dose, the bis-n-propyl spermine analogue DPSPM (4) diminished stooling by 74% (P<0.001), returning the stool output of the stressed rats to within error of the unstressed controls (P>0.1). At one-half the dose (11.6:mol/kg) the bis-n-butyl compound DBSPM (5) completely eliminated fecal output (P<0.001). Branching the n-propyl groups of 4 to DIPSPM (6) yielded a compound that, at the 11.6:mol/kg dose, substantially reduced stooling even more, from a 48% reduction observed with 4 to a 90% reduction with 6 (P<0.001). Even at one-half this dose, 5.8:mol/kg, stool output was reduced by 70% relative to the stressed controls (P<0.001) and was within error of the stool output of the unstressed animals (P>0.1). However, at the 11.6:mol/kg dose, the same branching change in 5 to DIBSPM (7) actually diminished activity at this dose, from a 100% decrease in fecal output with 5 to a 34% reduction with 7.

Removal of one of the isobutyl groups of 7 to generate MIBSPM (8) had little, if any, effect on activity. Adding a methylene to each of the terminal substituents of 7 to generate the corresponding pentyl analogue DIPESPM (9) had a minimal effect on activity at lower doses. Finally, the introduction of aromatic benzyl groups as in DBZSPM (10) or as in DTFMPhESPM (11) only served to diminish the activity relative to DESPM and DPSPM, respectively. However, the most remarkable of all of the (3,4,3) systems was CHX(3,4,3)-trans (12); a 100% reduction in fecal output was observed at a dose of 0.58:mol/kg (P<0.001), and a dose of 0.145:mol/kg reduced stool output by 80% (P<0.001), to a level within error of the unstressed controls (P>0.1). In addition, a 50% diminution in fecal output was observed at a dose of 0.07:mol/kg (P<005). When allometrically scaled, the dose of 0.07:mol/kg in the rat translates into a dose of only 0.3 mg for a 60-kg patient.

On expanding the methylene backbones from (3,3,3) systems (e.g., DENSPM) to (3,4,3) (e.g., DESPM) to (4,4,4) moieties (DEHSPM), there was an improvement in their anti-IBS activity (Table 1). However, further expansion of the backbone to a (5,4,5) base [DE(5,4,5), 14; PIP(5,4,5), 15] did not result in any enhancement of activity. Finally, to assess the importance of overall length of the molecules relative to how the methylene backbones are disposed, two unsymmetrical analogues [DE(3,3,6), 16; DIP(3,3,6), 17] were synthesized and evaluated. Interestingly, DE(3,3,6) has the same overall length as DEHSPM, but the former was less active. In keeping with the results from DIPSPM versus DESPM, DIP(3,3,6) was more active than was its diethyl counterpart (Table 1).

Because an orally active compound would be desirable for the treatment of IBS, selected analogues utilizing oral administration in the same model were assessed. In the initial studies animals were utilized that had been fasted overnight. Rodents were then given the drug of interest PO by gavage and stressed ½ h, 1 h, or 2 h post-drug. Unfortunately, because of the low baseline stool output in fasted control rats, the reductions in fecal output observed upon drug administration cannot be reported with any confidence (data not shown). Thereafter, only non-fasted animals were employed and were given the agents by gavage at doses of 11.6, 23.2, 57.8, or 115.6:mol/kg 30 minutes before initiating the stress. Of all of the compounds evaluated [DENSPM, DESPM, DIPSPM, CHX(3,4,3)-trans, DEHSPM, DE(5,4,5), and PIP(5,4,5)], only CHX(3,4,3)-trans, DEHSPM, and DE(5,4,5) showed any activity at all (Table 2). At doses of 11.6 and 23.2:mol/kg, CHX(3,4,3)-trans reduced stooling by about 80% (P=0.001 and <0.001, respectively). DEHSPM was effective at a dose of 115.6:mol/kg (40% diminution of fecal output; P<0.01), and DE(5,4,5) was active at doses of 23.2 and 57.8:mol/kg (55 and 73% reductions in fecal output, respectively; P<0.001 for both doses).

The acute toxicity of CHX(3,4,3)-trans IP in female CD-1 mice is about 150 mg/kg, and there is a strong neurological component to the toxic effects not apparent in DESPM- or DEHSPM-treated mice, which usually display a generalized depression with respiratory failure. At toxic doses (∃125 mg/kg, single dose), the CHX(3,4,3)-trans-treated mice, in addition to depression and respiratory failure, also displayed uncoordinated movements, intention tremors, and severe motor dysfunction, especially of the hind limbs. It is critical to point out that this dose, allometrically scaled, is at least 1000 times the dose of 0.0625 mg/kg needed to reduce fecal output of the stressed animals to that of the unstressed controls. However, signs of motor dysfunction, including seizures, have been observed in a rodent antidiarrheal model in rats treated with this drug at doses ∃1 mg/kg (Bergeron, R J et al., Polyamine Analogue Antidiarrheals: A Structure—Activity Study. A Med. Chem., Vol. 44, pages 232–244 (2001). The 1 mg/kg dose is, nevertheless, greater than 30 times the lowest dose (0.03125 mg/kg) that reduced stool output by >50% relative to the stressed controls. Thus, there is a large therapeutic window between a clinically effective dose in rats and a neurotoxic dose.

Signs of neurotoxicity similar to those described above in mice were observed in rats treated with DBSPM, DIBSPM, and DIPESPM at subtherapeutic doses equivalent to a 5 mg/kg dose of DEHSPM (Bergeron, supra). In the current study, the rats treated with DBSPM at doses of 11.6 or 57.8:mol/kg, or DIPESPM at a dose of 57.8:mol/kg were removed from the experiment after only 2 h (DBSPM) or 4.5 h (DIPESPM) due to severe neurotoxicity. In addition, all of the rats in the DBSPM 57.8:mol/kg group died within ~24 h post-dosing. Therefore, it seems that the longer, more lipophilic N-alkyl substituents result in increased neurotoxicity upon administration to animals.

Whereas the current guidelines for treating IBS primarily involve either managing psychological and psychosocial factors or altering a patient's diet, some pharmacological interventions have been marginally successful in treating IBS. These include antidepressants, codeine, the antimotility agent loperamide, and the bile salt-binding resin cholestyramine. Since some cases of IBS may be the result of abnormalities of intestinal motility and/or enhanced visceral sensitivity, it follows that those agents which alter intestinal motility would be beneficial to this subset of patients. Accordingly, we have exploited our previous experience in the development of polyamine analogue antidiarrheal agents to find analogues suitable for the treatment of diarrhea-predominant IBS.

The design concept was predicated on partitioning those structural components of the analogues responsible for the anti-IBS properties from those which are toxic. The alterations of the polyamine analogues fell into three categories: (a) changing the distance between the nitrogens and the overall length of the molecule, (b) keeping the overall length of the molecule the same but manipulating the ordering of the distance between the nitrogens, and (c) altering the terminal groups within a series of compounds possessing the same backbone. Expansion of the methylene backbones from (3,3,3) systems (e.g., DENSPM) that were completely ineffective upon SC administration to stressed rats, to (3,4,3) (e.g., DESPM), to (4,4,4) moieties (DEHSPM) resulted in improved anti-IBS activity; however, further expansion of the backbone to a (5,4,5) base did not result in any corresponding improvement of efficacy. The ordering and arrangement of the nitrogens within the methylene backbone seem to be critical to the compound's effectiveness; rearrangement of a (4,4,4) system to a (3,3,6) backbone of equal length actually reduced the activity in the rodent IIBS model.

The effects of manipulating the terminal alkyl groups on a particular backbone on the molecule's efficacy can be examined for several systems: (3,3,3) (DENSPM vs. DIPSPM), (3,3,6) [DE(3,3,6) vs. DIP(3,3,6)], and (3,4,3), which was the most thoroughly studied backbone in the present work. Changing the terminal diethyl groups of, e.g., DESPM, to isopropyl, e.g., DIPSPM, resulted in markedly improved efficacy. In fact, with the exception of the isobutyl- versus n-butyl spermines, the branched-chain analogues appeared to have increased activity when compared with their n-alkyl counterparts. This is in keeping with the observation that the branched-chain polyethyleneimines were highly active in inhibiting gastric emptying in rats, but the linear polyethyleneimine was not. However, the longer, more lipophilic N-alkyl substituents resulted in increased neurotoxicity when administered SC to the rats. In addition, the use of larger branched groups, e.g., isopentyl, did not enhance the activity of the spermine backbone; furthermore, the introduction of aromatic benzyl groups seemed to diminish the efficacy. However, in the end, the (3,4,3) analogue containing a cyclohexane ring in its center, CHX(3,4,3)-trans, is the most effective against stress-induced stooling, regardless of the mode of administration. This polyamine was also the most effective of the SPM analogues tested in the castor oil-induced diarrhea model. Although signs of motor dysfunction including seizures have been observed in a rodent antidiarrheal model in rats treated with this drug at doses ∃1 mg/kg, the 1 mg/kg dose is, nevertheless, greater than 30 times the lowest dose (0.03125 mg/kg) that reduced stool output by >50% relative to the stressed controls providing an acceptable therapeutic window.

TABLE 1

ACTIVITY OF POLYAMINE ANALOGUES AGAINST STRESS-INDUCED IRRITABLE BOWEL SYNDROME[a]

| Cmpd. No. | Structure/Abbreviation | Dose, kg⁻¹ mg | Dose, kg⁻¹ μmol | n | Stool Output[b] | P-Value[c] | % Reduction[d] |
|---|---|---|---|---|---|---|---|
| | Norspermines (3,3,3) | | | | | | |
| 1 | DENSPM | 0 | 0 | 5 | 12.4 ± 5.2 | — | — |
| | | 0.90 | 2.3 | 5 | 17.4 ± 5.1 | >0.05 | NS |
| | | 4.51 | 11.6 | 5 | 15.2 ± 4.5 | >0.05 | NS |
| | | 22.6 | 57.8 | 5 | 13.4 ± 5.9 | >0.05 | NS |
| 2 | DIPNSPM | 0 | 0 | 5 | 14.2 ± 7.6 | — | — |
| | | 0.97 | 2.3 | 5 | 17.6 ± 5.5 | >0.05 | NS |
| | | 4.8 | 11.6 | 5 | 13.6 ± 3.2 | >0.05 | NS |
| | | 24.2 | 57.8 | 5 | 7.4 ± 3.6 | >0.05 | NS |
| | Linear Spermine Analogues (3,4,3) | | | | | | |
| 3 | DESPM | 0 | 0 | 29 | 19.1 ± 6.4 | — | — |
| | | 9.3 | 23.2 | 15 | 12.5 ± 2.9 | <0.001 | 35 |
| | | 14 | 35.4 | 15 | 9.0 ± 6.3 | <0.001 | 53 |
| | | 24 | 61 | 5 | 2.8 ± 2.7 | <0.001 | 90 |
| 4 | DPSPM | 0 | 0 | 10 | 22.2 ± 11.3 | — | — |
| | | 1 | 2.3 | 5 | 11.4 ± 7.2 | <0.05 | 49 |
| | | 5 | 11.6 | 10 | 11.5 ± 8.7 | <0.05 | 48 |
| | | 10 | 23.2 | 10 | 5.7 ± 4.1 | <0.001 | 74 |
| | | 25 | 57.8 | 5 | 0.2 ± 0.4 | <0.001 | 99 |
| 5 | DBSPM | 0 | 0 | 5 | 22.8 ± 3.8 | — | — |
| | | 1.1 | 2.3 | 5 | 14.0 ± 4.8 | <0.01 | 39 |
| | | 5.3[e] | 11.6 | 5 | 0 ± 0 | <0.001 | 100 |
| | | 26.6[e,f] | 57.8 | 5 | 0 ± 0 | <0.001 | 100 |

TABLE 1-continued

ACTIVITY OF POLYAMINE ANALOGUES AGAINST STRESS-INDUCED IRRITABLE BOWEL SYNDROME[a]

| Cmpd. No. | Structure/Abbreviation | Dose, mg | Dose, $\mu mol\ kg^{-1}$ | n | Stool Output[b] | P-Value[c] | % Reduction[d] |
|---|---|---|---|---|---|---|---|
| 6 | DIPSPM | 0<br>2.5<br>5 | 0<br>5.8<br>11.6 | 5<br>5<br>5 | 15.6 ± 3.6<br>4.6 ± 2.3<br>1.6 ± 1.8 | —<br><0.001<br><0.001 | —<br>70<br>90 |
| 7 | DIBSPM | 0<br>1.1<br>5.3<br>10.7[g] | 0<br>2.3<br>11.6<br>23.2 | 10<br>10<br>10<br>10 | 18.4 ± 3.3<br>15.9 ± 5.7<br>12.2 ± 2.7<br>6.6 ± 3.1 | —<br>>0.05<br><0.001<br><0.001 | —<br>NS<br>34<br>64 |
| 8 | MIBSPM | 0<br>0.94<br>4.7<br>9.4[g] | 0<br>2.3<br>11.6<br>23.2 | 5<br>5<br>5<br>5 | 21.2 ± 4.4<br>14.8 ± 3.8<br>11.2 ± 2.2<br>10.6 ± 2.9 | —<br><0.05<br><0.005<br><0.005 | —<br>30<br>47<br>50 |
| 9 | DIPESPM | 0<br>1.1<br>5.7<br>28.2[h] | 0<br>2.3<br>11.6<br>57.8 | 5<br>5<br>5<br>5 | 17.4 ± 6.4<br>18.2 ± 2.8<br>14.6 ± 4.5<br>0 ± 0 | —<br>>0.05<br>>0.05<br><0.005 | —<br>NS<br>NS<br>100 |
| 10 | Cyclic Spermine Analogues (3,4,3)<br>DBZSPM | 0<br>1.2<br>6.1<br>30.5 | 0<br>2.3<br>11.6<br>57.8 | 5<br>5<br>5<br>5 | 18.6 ± 8.5<br>12.6 ± 4.8<br>11.6 ± 2.9<br>8.4 ± 1.5 | —<br>>0.05<br>>0.05<br><0.05 | —<br>NS<br>NS<br>55 |

TABLE 1-continued

ACTIVITY OF POLYAMINE ANALOGUES AGAINST STRESS-INDUCED IRRITABLE BOWEL SYNDROME[a]

| Cmpd. No. | Structure/Abbreviation | Dose, mg | Dose, $\mu$mol kg$^{-1}$ | n | Stool Output[b] | P-Value[c] | % Reduction[d] |
|---|---|---|---|---|---|---|---|
| 11 | <br>DTFMPhESPM | 0<br>1.6<br>8.0<br>16.0 | 0<br>2.3<br>11.6<br>23.2 | 5<br>5<br>5<br>5 | 16.2 ± 5.4<br>12.4 ± 2.1<br>13.6 ± 5.1<br>11.4 ± 2.1 | —<br>>0.05<br>>0.05<br>>0.05 | —<br>NS<br>NS<br>NS |
| 12 | 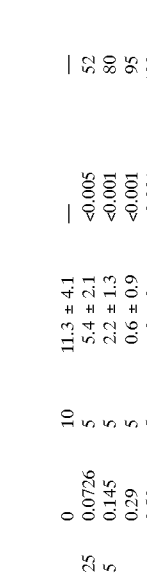<br>CHX(3,4,3)-trans | 0<br>0.03125<br>0.0625<br>0.125<br>0.25[g]<br>0.5[g]<br>0.99[g] | 0<br>0.0726<br>0.145<br>0.29<br>0.58<br>1.16<br>2.3 | 10<br>5<br>5<br>5<br>5<br>5<br>5 | 11.3 ± 4.1<br>5.4 ± 2.1<br>2.2 ± 1.3<br>0.6 ± 0.9<br>0 ± 0<br>0 ± 0<br>0 ± 0 | —<br><0.005<br><0.001<br><0.001<br><0.001<br><0.001<br><0.001 | —<br>52<br>80<br>95<br>100<br>100<br>100 |
|  | Longer Methylene Backbones |  |  |  |  |  |  |
| 13 | 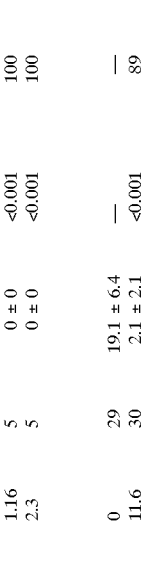<br>DEHSPM [DE(4,4,4)] | 0<br>5<br>25 | 0<br>11.6<br>57.8 | 29<br>30<br>5 | 19.1 ± 6.4<br>2.1 ± 2.1<br>0 ± 0 | —<br><0.001<br><0.001 | —<br>89<br>100 |
| 14 | 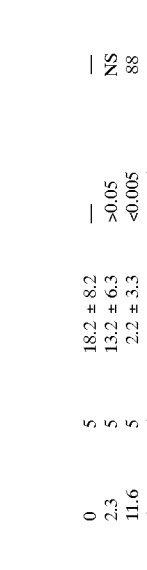<br>DE(5,4,5) | 0<br>1.1<br>5.3<br>26.6 | 0<br>2.3<br>11.6<br>57.8 | 5<br>5<br>5<br>5 | 18.2 ± 8.2<br>13.2 ± 6.3<br>2.2 ± 3.3<br>0 ± 0 | —<br>>0.05<br><0.005<br><0.005 | —<br>NS<br>88<br>100 |

TABLE 1-continued

ACTIVITY OF POLYAMINE ANALOGUES AGAINST STRESS-INDUCED IRRITABLE BOWEL SYNDROME[a]

| Cmpd. No. | Structure/Abbreviation | Dose, kg⁻¹ mg | Dose, kg⁻¹ μmol | n | Stool Output[b] | P-Value[c] | % Reduction[d] |
|---|---|---|---|---|---|---|---|
| 15 | PIP(5,4,5) | 0<br>1.06<br>5.28<br>26.38 | 0<br>2.32<br>11.57<br>57.8 | 5<br>5<br>5<br>5 | 11.0 ± 4.8<br>8.8 ± 1.6<br>8.2 ± 3.1<br>2.0 ± 2.0 | —<br>>0.05<br>>0.05<br><0.005 | —<br>NS<br>NS<br>82 |
| | *Unsymmetrical Methylene Backbones* | | | | | | |
| 16 | DE(3,3,6) | 0<br>1<br>5<br>25[i] | 0<br>2.31<br>11.56<br>57.5 | 5<br>5<br>5<br>5 | 13.2 ± 7.5<br>10.4 ± 5.2<br>9.4 ± 4.1<br>0.4 ± 0.9 | —<br>>0.05<br>>0.05<br><0.01 | —<br>NS<br>NS<br>97 |
| 17 | DIP(3,3,6) | 0<br>1.06[i]<br>5.32[i]<br>26.6[i] | 0<br>2.32<br>11.56<br>57.8 | 5<br>5<br>5<br>5 | 8.8 ± 5.0<br>1.4 ± 1.9<br>0 ± 0<br>0 ± 0 | —<br><0.05<br><0.01<br><0.01 | —<br>84<br>100<br>100 |

[a]Polyamine analogues were administered SC to rats at the doses shown in the table. Thirty minutes later, the rats were subjected to stress, i.e., a cage filled with water to within 0.5 cm of the height of a 70 × 50 mm dish. Stool output was monitored for 6 h after commencement of the stress.
[b]Stool output is expressed as the number of fecal pellets excreted over the 6-h collection period.
[c]A one-tailed t-test assuming unequal variance was performed on the data of the treated vs control (0 mg/kg) animals for each compound. A value of $P < 0.05$ was considered significant.
[d]Percent reduction was calculated by dividing the mean value from the treated animals (T) by the mean value from the control animals (C), subtracting the resulting quotient from 1.0, and multiplying by 100 [i.e., (1.0-T/C) × 100]. NS, not significant.
[e]Due to severe CNS toxicity, the experiment was stopped after 2 h; the results after 2 h are reported.
[f]All rats in this group died ~24 h after drug administration.
[g]Toxic effects were evident, including huddling in the corner of the cage.
[h]Due to severe CNS toxicity, 3 of the 5 rats were removed after 4–4.5 h; neither of the remaining 2 rats had any stool output for the remainder of the study.
[i]The rats were quite lethargic, as though sedated, after drug administration.

TABLE 2

ACTIVITY OF POLYAMINE ANALOGUES WHEN GIVEN ORALLY TO RATS[a]

| Compound | Dose, kg$^{-1}$ mg | Dose, kg$^{-1}$ μmol | n | Stool Output[b] | P-Value[c] | % Reduction[d] |
|---|---|---|---|---|---|---|
| CHX(3,4,3)-trans | 0 | 0 | 5 | 10.0 ± 2.9 | — | — |
| | 1 | 2.3 | 5 | 9.0 ± 1.6 | >0.05 | NS |
| | 5 | 11.6 | 5 | 2.2 ± 1.3 | 0.001 | 78 |
| | 10 | 23.2 | 5 | 2.0 ± 1.9 | <0.001 | 80 |
| DEHSPM | 0 | 0 | 5 | 17.6 ± 3.9 | — | — |
| | 50 | 115.6 | 5 | 10.6 ± 1.8 | <0.01 | 40 |
| DE(5,4,5) | 0 | 0 | 10 | 19.1 ± 3.3 | — | — |
| | 5.3 | 11.6 | 10 | 15.2 ± 8.5 | >0.05 | NS |
| | 10.6 | 23.2 | 10 | 8.6 ± 4.9 | <0.001 | 55 |
| | 26.6 | 57.8 | 10 | 5.1 ± 3.1 | <0.001 | 73 |

[a]Polyamine analogues were administered to rats PO by gavage at the doses shown in the table. Thirty minutes later, the rats were subjected to stress, i.e., a cage filled with water to within 0.5 cm of the height of a 70 × 50 mm dish. Stool output was monitored for 6 hr after commencement of the stress.
[b]Stool output is expressed as the number of fecal pellets excreted over the 6-hr collection period.
[c]A one-tailed t-test assuming unequal variance was performed on the data of the treated vs control (0 mg/kg) animals for each compound. A value of $P < 0.05$ was considered significant.
[d]Percent reduction was calculated by dividing the mean value from the treated animals (T) by the mean value from the control animals (C), subtracting the resulting quotient from 1.0, and multiplying by 100 [i.e., (1.0-T/C) × 100].
NS, not significant.

It is thus established, therefore, that the compounds described herein are useful for the treatment of irritable bowel disease (IBD) or syndrome (IBS).

The method and composition of the present invention are predicated on administering to a subject (human or animal) suffering from irritable bowel disease an effective amount of one or more of the compounds described herein as being effective therefore. Administration may be accomplished either therapeutically or prophylactically by means of pharmaceutical compositions which are prepared by techniques well known in the pharmaceutical sciences.

While the compounds of the invention are preferably administered orally or intrarectally, they may also be administered by a variety of other routes such as transdermally, subcutaneously, intranasally, intramuscularly and intravenously. The present invention is also directed to pharmaceutical compositions which include at least one compound as described above in association with one or more pharmaceutically acceptable diluents, excipients or carriers therefor. In making the pharmaceutical compositions of the present invention, one or more compounds will usually be mixed with, diluted by or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 60% by weight of active compound, soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The dose of the compound is that amount effective to prevent occurrence of the symptoms of the disease or to treat some symptoms of the disease from which the patient suffers. By "effective amount," "therapeutic amount" or "effective dose" is meant that amount sufficient to elicit the desired pharmacological or therapeutic effects, thus resulting in effective prevention or treatment of the disease. Prevention of the disease is manifested by a prolonging or delaying of the onset of the symptoms of the disease. Treatment of the disease is manifested by a decrease in the symptoms associated with the disease or an amelioration of the recurrence of the symptoms of the disease.

The effective dose may vary, depending upon factors such as the condition of the patient, the severity of the symptoms of the disease and the manner in which the pharmaceutical composition is administered. The compositions are formulated, preferably in a unit dosage form, such that each dosage contains from about 0.006 to about 12,000 mg, more usually about 0.06 to about 6,000 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more of the above-described suitable pharmaceutical diluents, excipients or carriers.

The compounds are effective over a wide dosage range in treating IBD. Thus, as used herein, the term "effective amount" refers to a dosage range of from about 0.006 to about 500 mg/kg of body weight per day. In the treatment of adult humans, the range of about 0.06 to about 250 mg/kg, in single or divided doses, is preferred. However, it will be understood that the amount of compound actually administered will be determined by a physician in light of the relevant circumstances, including (1) the condition to be treated, (2) the choice of compound to be administered, (3) the chosen route of administration, (4) the age, weight and response of the individual patient, and (5) the severity of the patient's symptoms. Therefore, the above dosage ranges are not intended to limit the scope of the invention in any way.

By "active ingredient" is meant a polyamine as described herein or a salt thereof with a pharmaceutically acceptable acid. By "salt" is meant an addition salt between the polyamine of the invention and a sufficient amount of pharmacologically appropriate acid, such as hydrochloric, sulfuric, phosphoric, acetic, butyric, citric, maleic, lactic, valeric, tartaric, gluconic, succinic and the like, made by conventional chemical means.

What is claimed is:

1. A method for treating irritable bowel syndrome in a subject in need of such treatment, comprising administering to said subject amounts of at least two polyamines effective to treat irritable bowel syndrome in said subject, said polyamines being selected from the group consisting of polyamines having the formula:

R—NH—(CH$_2$)$_a$—NH—(CH$_2$)$_b$NH—(CH$_2$)$_c$—NH$_2$,   1)

CF$_3$—C$_6$H$_5$—(CH$_2$)$_a$—NH—(CH$_2$)$_b$—NH—(CH$_2$)$_c$—NH—(CH$_2$)$_d$—NH—(CH$_2$)$_e$—C$_6$H$_5$—CF$_3$,   2)

R—NH—(CH$_2$)$_a$—NH—C$_6$H$_6$—NH—(CH$_2$)$_b$—NH—R and   3)

PIP—(CH$_2$)$_a$NH—(CH$_2$)$_b$—NH—(CH$_2$)$_c$—PIP,   4)

wherein:
R is alkyl, aryl, aralkyl, alkaryl, or cyclo-alkyl having up to about 10 carbon atoms, and any of said alkyl chains may optionally be interrupted by at least one etheric oxygen atom,
PIP is piperidine and
a, b, c, d, and e may be the same or different and are integers from 1–10.

2. The method of claim 1 wherein said subject is human.

3. The method according to claim 1, wherein said polyamines are administered at a dose between about 0.0001 mg/day and about 500 mg/day.

4. The method according to claim 1, wherein said polyamines are administered in one or more forms selected from the group consisting of orally, parenterally, transdermally, or by suppository.

5. The method according to claim 1, wherein said polyamine is administered orally.

6. The method according to claim 1, wherein said polyamine is administered parenterally.

7. A pharmaceutical composition in unit dosage form adapted for administration to a subject suffering from irritable bowel syndrome comprising amounts of at least two polyamines therapeutically effective to treat irritable bowel syndrome and a pharmaceutically acceptable carrier therefore, said polyamine being selected from the group consisting of polyamines having the formula:

R—NH—(CH$_2$)$_a$—NH—(CH$_2$)$_b$NH—(CH$_2$)$_c$—NH$_2$,   1)

CF$_3$—C$_6$H$_5$—(CH$_2$)$_a$—NH—(CH$_2$)$_b$—NH—(CH$_2$)$_c$—NH—(CH$_2$)$_d$—NH—(CH$_2$)$_e$—C$_6$H—CF$_3$,   2)

R—NH—(CH$_2$)$_a$—NH—C$_6$H$_6$—NH—(CH$_2$)$_b$—NH—R and   3)

PIP—(CH$_2$)$_a$NH—(CH$_2$)$_b$—NH—(CH$_2$)$_c$—PIP,   4)

wherein:
R is alkyl, aryl, aralkyl, alkaryl, or cyclo-alkyl having up to 10 about carbon atoms, and any of said alkyl chains may optionally be interrupted by at least one etheric oxygen atom,
PIP is piperidine and
a, b, c, d, and e may be the same or different and are integers from 1–10.

8. The composition according to claim 7 wherein the form thereof is such that it may be administered orally, parenterally, transdermally, or by suppository.

9. The composition according to claim 7 wherein the form thereof is such that it may be administered orally.

10. The composition according to claim 7 wherein the form thereof is such that it may be administered parenterally.

11. An article of manufacture comprising packaging material and at least two pharmaceutical agents contained within said packaging material, wherein said pharmaceutical agents are effective for the treatment of a subject suffering from irritable bowel syndrome, and wherein said packaging material comprises a label which indicates that said pharmaceutical agents can be used for ameliorating the symptoms associated with irritable bowel syndrome, and wherein said pharmaceutical agents are selected from the group consisting of polyamines having the formula:

R—NH—(CH$_2$)$_a$—NH—(CH$_2$)$_b$NH—(CH$_2$)$_c$—NH$_2$,   1)

CF$_3$—C$_6$H$_5$—(CH$_2$)$_a$—NH—(CH$_2$)$_b$—NH—(CH$_2$)$_c$—NH—(CH$_2$)$_d$—NH—(CH$_2$)$_e$—C$_6$H$_5$—CF$_3$,   2)

R—NH—(CH$_2$)$_a$—NH—C$_6$H$_6$—NH—(CH$_2$)$_b$—NH—R and   3)

PIP—(CH$_2$)$_a$NH—(CH$_2$)$_b$—NH—(CH$_2$)$_c$—PIP,   4)

wherein:
R is alkyl, aryl, aralkyl, alkaryl, or cyclo-alkyl having up to about 10 carbon atoms, and any of said alkyl chains may optionally be interrupted by at least one etheric oxygen atom,
PIP is piperidine and
a, b, c, d, and e may be the same or different and are integers from 1–10.

* * * * *